United States Patent
Asahi et al.

(10) Patent No.: US 9,566,085 B2
(45) Date of Patent: Feb. 14, 2017

(54) FLUID EJECTION DEVICE

(71) Applicant: SEIKO EPSON CORPORATION, Tokyo (JP)

(72) Inventors: Tsunemori Asahi, Azumino (JP); Masaki Gomi, Hino (JP); Kazuaki Uchida, Fujimi-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 87 days.

(21) Appl. No.: 14/683,030

(22) Filed: Apr. 9, 2015

(65) Prior Publication Data

US 2015/0289900 A1    Oct. 15, 2015

(30) Foreign Application Priority Data

Apr. 10, 2014    (JP) .................. 2014-080827

(51) Int. Cl.
*A61B 17/3203* (2006.01)
*A61M 3/02* (2006.01)
(Continued)

(52) U.S. Cl.
CPC .......... *A61B 17/3203* (2013.01); *A61M 3/02* (2013.01); *A61M 5/1452* (2013.01); *A61M 5/14224* (2013.01); *A61M 5/14586* (2013.01); *A61M 5/1684* (2013.01); *A61M 39/08* (2013.01); *A61M 39/22* (2013.01); *A61B 2017/00017* (2013.01); *A61B 2017/00022* (2013.01); *A61B 2217/007* (2013.01); *A61M 5/1458* (2013.01);
(Continued)

(58) Field of Classification Search
CPC ............... A61B 17/3203; A61B 17/32037; A61B 2017/32032; A61B 2017/32035; A61M 2205/3334; A61M 2205/3389; A61M 3/0233; A61M 3/0237; A61M 3/025; A61M 3/0254; A61M 3/0258; A61M 3/0262
See application file for complete search history.

(56) References Cited

U.S. PATENT DOCUMENTS 5,259,842 A * 11/1993 Plechinger .......... A61B 17/3203
                                                       222/334
5,505,729 A *  4/1996 Rau .................... A61B 17/3203
                                                       604/22
(Continued)

FOREIGN PATENT DOCUMENTS

JP      2003-500098 A    1/2003
JP      2013-213422 A   10/2013

*Primary Examiner* — Ryan J Severson
(74) *Attorney, Agent, or Firm* — Maschoff Brennan

(57) ABSTRACT

A fluid ejection device includes: a fluid ejection unit that ejects a fluid in a pulsed manner; a fluid accommodation portion that accommodates the fluid at a predetermined pressure or higher; a fluid supply unit that supplies the fluid accommodated in the fluid accommodation portion to the fluid ejection unit; a connection channel that connects the fluid ejection unit and the fluid accommodation portion, and acts as a channel through which the fluid flows; an opening and closing unit that opens and closes the connection channel; and a control unit that sends an open signal for opening the connection channel to the opening and closing unit, and sends an ejection signal for ejecting the fluid to the fluid ejection unit. The control unit sends the ejection signal after a predetermined amount of time has elapsed from the sending of the open signal.

6 Claims, 9 Drawing Sheets

(51) Int. Cl.
   *A61M 39/22*     (2006.01)
   *A61M 39/08*     (2006.01)
   *A61M 5/145*     (2006.01)
   *A61M 5/168*     (2006.01)
   *A61M 5/142*     (2006.01)
   *A61B 17/00*     (2006.01)

(52) U.S. Cl.
   CPC . *A61M 2205/0294* (2013.01); *A61M 2205/14* (2013.01); *A61M 2205/332* (2013.01); *A61M 2205/3334* (2013.01); *A61M 2205/3382* (2013.01); *A61M 2205/3386* (2013.01); *A61M 2205/3389* (2013.01); *A61M 2206/10* (2013.01); *A61M 2206/20* (2013.01)

(56)                References Cited

U.S. PATENT DOCUMENTS

| Patent/Pub No. | Kind | Date | Inventor | Class |
|---|---|---|---|---|
| 5,871,462 | A * | 2/1999 | Yoder | A61B 17/1644 604/22 |
| 7,278,721 | B2 * | 10/2007 | Shimizu | B41J 2/17546 347/49 |
| 7,942,489 | B2 * | 5/2011 | Ushinohama | B41J 2/04505 347/10 |
| 8,382,702 | B2 * | 2/2013 | Uchida | A61B 17/3203 604/118 |
| 8,919,664 | B2 * | 12/2014 | Seto | A61B 17/3203 239/101 |
| 9,005,227 | B2 * | 4/2015 | Kojima | A61B 17/3203 606/167 |
| 9,168,056 | B2 * | 10/2015 | Uchida | A61B 17/3203 |
| 9,174,435 | B2 * | 11/2015 | Yoshino | B41J 2/04541 |
| 9,204,890 | B2 * | 12/2015 | Asahi | A61B 17/3203 |
| 9,237,901 | B2 * | 1/2016 | Asahi | A61B 17/3203 |
| 9,238,373 | B2 * | 1/2016 | Gomi | B41J 2/17596 |
| 9,248,654 | B2 * | 2/2016 | Gomi | B41J 2/175 |
| 9,296,213 | B2 * | 3/2016 | Gomi | A61B 17/3203 |
| 9,352,082 | B2 * | 5/2016 | Uchida | A61M 5/1422 |
| 9,352,574 | B2 * | 5/2016 | Gomi | B41J 2/175 |
| 9,402,946 | B2 * | 8/2016 | Seto | A61B 17/3203 |
| 2002/0045911 | A1 | 4/2002 | Fletcher et al. | |
| 2005/0244301 | A1 | 11/2005 | Fletcher et al. | |
| 2008/0214890 | A1 * | 9/2008 | Motai | A61B 1/00135 600/107 |
| 2009/0043480 | A1 * | 2/2009 | Seto | A61B 17/3203 701/103 |
| 2010/0078495 | A1 * | 4/2010 | Seto | A61B 17/3203 239/1 |
| 2010/0245495 | A1 * | 9/2010 | Katada | B41J 2/515 347/85 |
| 2011/0006127 | A1 * | 1/2011 | Ono | A61B 17/3203 239/1 |
| 2011/0036859 | A1 * | 2/2011 | Matsuzaki | A61B 17/3203 604/131 |
| 2011/0054505 | A1 * | 3/2011 | Kojima | A61B 17/3203 606/167 |
| 2011/0194945 | A1 * | 8/2011 | Kensy | A61B 17/3203 417/26 |
| 2011/0208224 | A1 * | 8/2011 | Kojima | F04B 43/04 606/167 |
| 2012/0046605 | A1 * | 2/2012 | Uchida | A61B 17/3203 604/65 |
| 2012/0095401 | A1 * | 4/2012 | Uchida | A61B 17/3203 604/151 |
| 2012/0176431 | A1 * | 7/2012 | Kojima | A61B 17/3203 347/14 |
| 2012/0181352 | A1 * | 7/2012 | Seto | A61B 17/3203 239/101 |
| 2013/0038654 | A1 * | 2/2013 | Yoshino | B41J 2/04541 347/10 |
| 2013/0064698 | A1 * | 3/2013 | Oshima | F04B 43/046 417/410.1 |
| 2013/0096601 | A1 * | 4/2013 | Asahi | A61B 17/3203 606/190 |
| 2013/0144321 | A1 * | 6/2013 | Uchida | A61B 17/3203 606/190 |
| 2013/0158544 | A1 * | 6/2013 | Kuhner | A61B 17/3203 606/39 |
| 2013/0243616 | A1 * | 9/2013 | Seto | F04B 43/095 417/212 |
| 2014/0127037 | A1 * | 5/2014 | Uchida | F04B 11/005 417/53 |
| 2014/0134001 | A1 * | 5/2014 | Uchida | A61M 5/1422 417/53 |
| 2014/0296892 | A1 * | 10/2014 | Uchida | B05B 5/16 606/167 |
| 2014/0296896 | A1 * | 10/2014 | Kojima | A61B 17/3203 606/167 |
| 2015/0073453 | A1 * | 3/2015 | Kojima | A61B 17/3203 606/167 |
| 2015/0075367 | A1 * | 3/2015 | Seto | A61B 17/3203 92/96 |
| 2015/0238216 | A1 * | 8/2015 | Uchida | A61B 17/3203 606/167 |
| 2015/0282830 | A1 * | 10/2015 | Miyazaki | A61B 17/3203 606/167 |
| 2015/0283809 | A1 * | 10/2015 | Miyazaki | B41J 2/04551 347/47 |
| 2015/0289894 | A1 * | 10/2015 | Miyazaki | A61B 17/3203 606/170 |
| 2015/0289895 | A1 * | 10/2015 | Gomi | A61B 17/3203 606/167 |
| 2015/0289896 | A1 * | 10/2015 | Gomi | A61B 17/3203 606/167 |
| 2015/0289897 | A1 * | 10/2015 | Gomi | A61B 17/3203 606/167 |
| 2015/0289898 | A1 * | 10/2015 | Gomi | A61B 17/3203 606/170 |
| 2015/0289899 | A1 * | 10/2015 | Asahi | A61B 17/3203 606/167 |
| 2015/0289900 | A1 * | 10/2015 | Asahi | A61B 17/3203 606/167 |
| 2015/0290933 | A1 * | 10/2015 | Asahi | A61B 17/3203 347/9 |
| 2015/0290942 | A1 * | 10/2015 | Gomi | A61B 17/3203 347/85 |
| 2015/0290943 | A1 * | 10/2015 | Gomi | B41J 2/175 347/85 |
| 2015/0290944 | A1 * | 10/2015 | Gomi | B41J 2/175 347/7 |
| 2015/0290949 | A1 * | 10/2015 | Gomi | B41J 2/17596 347/85 |
| 2015/0293538 | A1 * | 10/2015 | Asahi | A61B 17/3203 700/283 |
| 2016/0008021 | A1 * | 1/2016 | Yoshino | B41J 2/04541 606/167 |
| 2016/0081707 | A1 * | 3/2016 | Asahi | A61B 17/3203 606/167 |
| 2016/0129689 | A1 * | 5/2016 | Gomi | B41J 2/175 347/9 |
| 2016/0242801 | A1 * | 8/2016 | Gomi | B41J 2/175 |

* cited by examiner

FLUID EJECTION DEVICE

This application claims the benefit of Japanese patent application No. 2014-080827, filed on Apr. 10, 2014. The content of the aforementioned application is incorporated herein by reference in its entirety.

BACKGROUND

1. Technical Field

The present invention relates to a fluid ejection device that ejects a fluid in a pulsed manner.

2. Related Art

In the related art, a fluid ejection device that incises or excises living tissues by ejecting a fluid in a pulsed manner at a high speed is known in the medical field. The following are examples of the fluid ejection device: a fluid ejection device (refer to JP-A-2013-213422) configured to include a fluid chamber, the volume of which is changed via the driving of a volume varying unit, a pulsation generator that ejects the fluid in a pulsed manner at a high speed, a fluid supply unit that supplies a fluid to the pulsation generator, and a connection tube, through which the pulsation generator and the fluid supply unit communicate with each other; and a fluid ejection device configured to include a vapor generation unit in a chamber, and to eject the fluid in a pulsed manner by using high pressure vapor bubbles generated by the vapor generation unit (refer to JP-T-2003-500098).

Meanwhile, the fluid ejection device in the related art ejects the fluid in a pulsed manner from a fluid ejection unit at the same time as opening a connection channel from the fluid supply unit to the fluid ejection unit. FIG. 11 illustrates a change in the pressure of the fluid ejected by the fluid ejection device in the related art.

From FIG. 11, it is known that when the connection channel is opened at a time of t, and concurrently, the fluid is ejected in a pulsed manner, pressure applied to the fluid increases temporarily. The high pressure causes a temporary high ejection force unintended by a practitioner.

SUMMARY

An advantage of some aspects of the invention is to provide a fluid ejection device that ejects a fluid while reducing a high ejection force originating from a temporary pressure increase.

A fluid ejection device according to an aspect of the invention includes: a fluid ejection unit that ejects a fluid in a pulsed manner; a fluid accommodation portion that accommodates the fluid at a predetermined pressure or higher; a fluid supply unit that supplies the fluid accommodated in the fluid accommodation portion to the fluid ejection unit; a connection channel that connects the fluid ejection unit and the fluid accommodation portion, and acts as a channel through which the fluid flows; an opening and closing unit that opens and closes the connection channel; and a control unit that sends an open signal for opening the connection channel to the opening and closing unit, and sends an ejection signal for ejecting the fluid to the fluid ejection unit. The control unit sends the ejection signal after a predetermined amount of time has elapsed from the sending of the open signal.

Other features of the invention will be made apparent by the description of this specification and the accompanying drawings.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an embodiment of the invention will be described with reference to the accompanying drawings. A fluid ejection device according to the embodiment can be used in various procedures such as the cleaning or cutting of a fine object or structure, living tissue, or the like; however, an example of the embodiment given in the following description is the fluid ejection device suitable for use as an operation scalpel to incise or excise living tissue. Accordingly, a fluid used in the fluid ejecting device according to the embodiment is water, physiologic saline, a predetermined fluid medicine, or the like. The drawings referenced in the following description are schematic views in which a portion or a member is vertically and horizontally scaled differently from an actual scale for illustrative purposes.

First Embodiment

Entire Configuration

Figure 1:
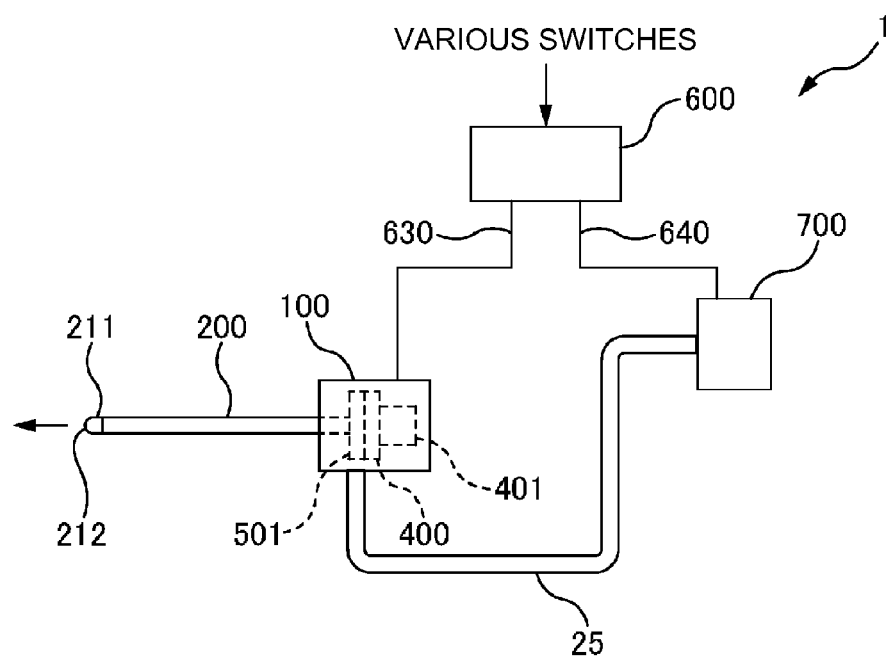
FIG. 1 is a block diagram illustrating an example of the entire configuration of a fluid ejection device according to an embodiment of the invention.

FIG. 1 is a view illustrating the configuration of a fluid ejection device 1 as an operation scalpel according to the embodiment. The fluid ejection device 1 according to the embodiment includes a pump 700 for supplying a fluid; a fluid ejection unit 100 that converts a flow of the fluid supplied from the pump 700 into a pulsed flow, and ejects the fluid in a pulsed manner; a drive control unit 600 that controls the fluid ejection device 1 in cooperation with the pump 700; and a connection tube 25 acting as a connection path through which the pump 700 and the fluid ejection unit 100 are connected to each other, and the fluid flows. The fluid ejection device 1 according to the embodiment includes two control units which are the drive control unit 600 and a pump control unit 710 (to be described later); however, the fluid ejection device 1 may include one control unit or a plurality of control units.

The fluid ejection unit 100 includes a fluid chamber 501 that accommodates the fluid supplied from the pump 700; a diaphragm 400 that changes the volume of the fluid chamber 501; and a piezoelectric element 401 that vibrates the diaphragm 400, all of which will be described later in detail.

The fluid ejection unit 100 includes a thin pipe-like fluid ejection tube 200 that acts as a channel of the fluid discharged from the fluid chamber 501, and a nozzle 211 that is mounted on a tip end portion of the fluid ejection tube 200 and has a reduced channel diameter.

The fluid ejection unit 100 converts a flow of the fluid into a pulsed flow and ejects the fluid in a pulsed manner at a high speed via the fluid ejection tube 200 and the nozzle 211 by driving the piezoelectric element 401 in response to an ejection signal output from the drive control unit 600 and changing the volume of the fluid chamber 501.

The drive control unit 600 and the fluid ejection unit 100 are connected to each other via a control cable 630, and the ejection signal for driving the piezoelectric element 401 output from the drive control unit 600 is transmitted to the fluid ejection unit 100 via the control cable 630.

The drive control unit 600 and the pump 700 are connected to each other via a communication cable 640, and the drive control unit 600 and the pump 700 transmit and receive various commands or data therebetween according to a predetermined communication protocol such as a controller area network (CAN).

The drive control unit 600 receives signals from various switches operated by a practitioner who performs an operation using the fluid ejection unit 100, and controls the pump 700 or the fluid ejection unit 100 via the control cable 630 or the communication cable 640.

The switches that input signals to the drive control unit 600 are a fluid ejection unit start-up switch 625, an ejection intensity switching switch 627, a flushing switch 628, and the like (not illustrated).

The fluid ejection unit start-up switch 625 is a switch for switching between the ejection and the non-ejection of the fluid from the fluid ejection unit 100. When a practitioner who performs an operation using the fluid ejection unit 100 operates the fluid ejection unit start-up switch 625, the drive control unit 600 controls the fluid ejection unit 100 to eject the fluid or stop the ejection of the fluid in cooperation with the pump 700. The fluid ejection unit start-up switch 625 can be a switch configured to be operated by the practitioner's feet, or a switch that is provided integrally with the fluid ejection unit 100 grasped by the practitioner, and configured to be operated by the practitioner's hands or fingers.

The ejection intensity switching switch 627 is a switch for changing the intensity of fluid ejection from the fluid ejection unit 100. When the ejection intensity switching switch 627 is operated, the drive control unit 600 controls the fluid ejection unit 100 and the pump 700 so as to increase and decrease the intensity of fluid ejection.

The flushing switch 628 will be described later.

In the embodiment, a pulsed flow implies a flow of a fluid, a flow direction of which is constant, and the flow rate or flow speed of which is changed periodically or non-periodically. The pulsed flow may be an intermittent flow in which the flowing and stopping of the fluid are repeated; however, since the flow rate or flow speed of the fluid is preferably changed periodically or non-periodically, the pulsed flow is not necessarily an intermittent flow.

Similarly, the ejection of a fluid in a pulsed form implies the ejection of the fluid by which the flow rate or moving speed of an ejected fluid is changed periodically or non-periodically. An intermittent ejection is described as an example of the pulsed ejection, in which the ejection and the non-ejection of the fluid are repeated; however since a flow rate or a moving speed of an ejected fluid may be changed periodically or non-periodically, the type of the ejection is not necessarily the intermittent ejection.

When the driving of the fluid ejection unit 100 is stopped, that is, when the volume of the fluid chamber 501 is not changed, the fluid supplied from the pump 700 as a fluid supply unit at a predetermined pressure continuously flows out of the nozzle 211 via the fluid chamber 501.

The fluid ejection device 1 according to the embodiment may be configured to include a plurality of the pumps 700. For example, FIG. 2 illustrates an example in which the fluid ejection device 1 is configured to include two pumps 700.

Figure 2:
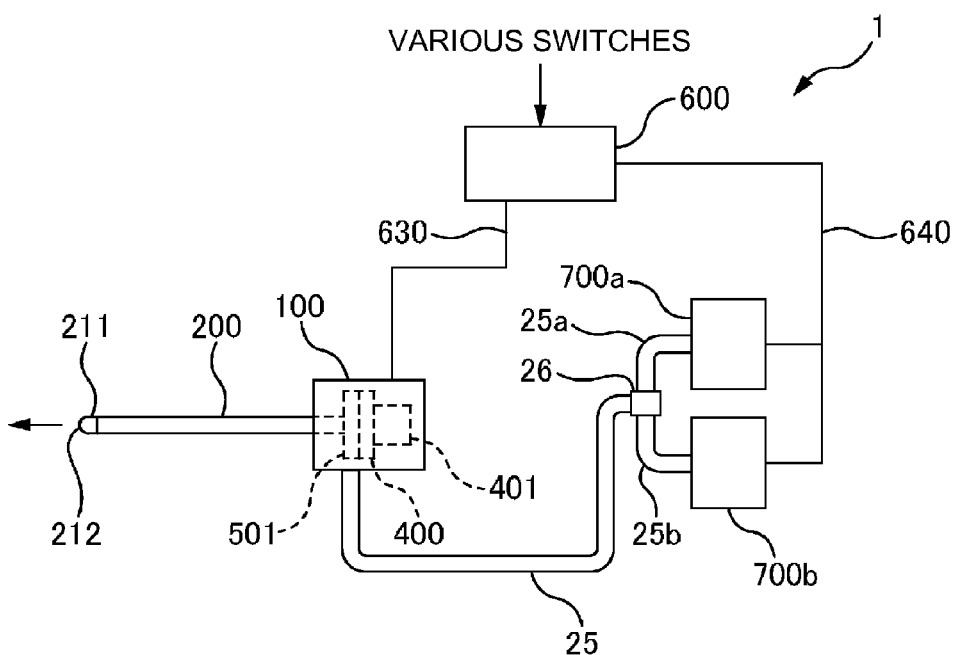
FIG. 2 is a block diagram illustrating another example of the entire configuration of the fluid ejection device according to the embodiment of the invention.

In this case, as illustrated in FIG. 2, the fluid ejection device 1 includes a first pump 700*a* and a second pump 700*b*. A first connection tube 25*a*, a second connection tube 25*b*, the connection tube 25, and a three way stopcock 26 form a connection path which connects the fluid ejection unit 100 and the first pump 700*a* and the fluid ejection unit 100 and the second pump 700*b*, and through which the fluid flows.

The three way stopcock 26 is a valve configured to be able to communicate the first connection tube 25*a* and the connection tube 25, or the second connection tube 25*b* and the connection tube 25, and either one of the first pump 700*a* and the second pump 700*b* is selectively used.

In this configuration, for example, when the first pump 700*a* cannot supply the fluid for unknown reasons such as a malfunction while being selected and used, it is possible to continuously use the fluid ejection device 1 and to minimize adverse effects associated with the non-supply of the fluid from the first pump 700*a* by switching the three way stopcock 26 so as to communicate the second connection tube 25*b* and the connection tube 25, and starting the supply of the fluid from the second pump 700*b*.

When the fluid ejection device 1 is configured to include a plurality of the pumps 700, but the pumps 700 are not required to be distinctively described, in the following description, the pumps 700 are collectively expressed by the pump 700.

In contrast, when the plurality of pumps 700 are required to be distinctively described, suffixes such as "a" and "b" are properly added to reference sign 700 of the pump, and each of the pumps 700 is distinctively expressed by the first pump 700*a* or the second pump 700*b*. In this case, each configuration element of the first pump 700*a* is expressed by adding the suffix "a" to a reference sign of each configuration element, and each configuration element of the second pump 700*b* is expressed by adding the suffix "b" to a reference sign of each configuration element.

Pump

Subsequently, an outline of the configuration and operation of the pump 700 according to the embodiment will be described with reference to FIG. 3.

The pump 700 according to the embodiment includes the pump control unit 710; a slider 720; a motor 730; a linear guide 740; and a pinch valve 750. The pump 700 is configured to have a fluid container mounting unit 770 for attachably and detachably mounting a fluid container 760 that accommodates the fluid. The fluid container mounting unit 770 is formed so as to hold the fluid container 760 at a specific position when the fluid container 760 is mounted thereon.

The following switches (which will be described later in detail) (not illustrated) input signals to the pump control unit 710: a slider release switch 780; a slider set switch 781; a fluid supply ready switch 782; a priming switch 783; and a pinch valve switch 785.

In the embodiment, for example, the fluid container 760 is formed of a medical syringe configured to include a syringe 761 and a plunger 762.

In the fluid container 760, a protrusive cylinder-shaped opening 764 is formed in a tip end portion of the syringe 761. When the fluid container 760 is mounted on the fluid container mounting unit 770, an end portion of the connection tube 25 is inserted into the opening 764, and a fluid channel is formed from the inside of the syringe 761 to the connection tube 25.

The pinch valve 750 is a valve as an example of an opening and closing unit that is provided on a path of the connection tube 25 and opens and closes a fluid channel between the fluid container 760 and the fluid ejection unit 100.

The pump control unit 710 controls the opening and closing of the pinch valve 750. When the pump control unit 710 opens the pinch valve 750, the fluid container 760 and the fluid ejection unit 100 communicate with each other via the channel therebetween. When the pump control unit 710 closes the pinch valve 750, the channel between the fluid container 760 and the fluid ejection unit 100 is shut off.

In a state where the fluid container 760 is mounted on the fluid container mounting unit 770, and the pinch valve 750 is opened, when the plunger 762 of the fluid container 760 moves in a direction (hereinafter, also referred to as a push-in direction) in which the plunger 762 is pushed into the syringe 761, the volume of a space (hereinafter, also referred to as a fluid accommodation portion 765) is reduced, the space being enveloped by an end surface of a gasket 763 made of resin such as elastic rubber and mounted at the tip of the plunger 762 in the push-in direction, and an inner wall of the syringe 761, and the fluid in the fluid accommodation portion 765 is discharged via the opening 764 of the tip end portion of the syringe 761. The connection tube 25 is filled with the fluid discharged via the opening 764, and the discharged fluid is supplied to the fluid ejection unit 100.

In contrast, in a state where the fluid container 760 is mounted on the fluid container mounting unit 770, and the pinch valve 750 is closed, when the plunger 762 of the fluid container 760 moves in the push-in direction, it is possible to reduce the volume of the fluid accommodation portion 765, the fluid accommodation portion 765 being enveloped by the gasket 763 mounted at the tip of the plunger 762 and the inner wall of the syringe 761, and it is possible to increase the pressure of the fluid in the fluid accommodation portion 765.

The pump control unit 710 moves the slider 720 along a direction (in the push-in direction and the opposite direction of the push-in direction) in which the plunger 762 moves in a state where the fluid container 760 is mounted on the fluid container mounting unit 770, and the plunger 762 moves in accordance with the movement of the slider 720.

Specifically, the slider 720 as an example of a pressurizing unit is attached to the linear guide 740 in such a manner that a pedestal 721 of the slider 720 engages with a rail (not illustrated) formed linearly on the linear guide 740 along the slide direction of the plunger 762. The linear guide 740 moves the pedestal 721 of the slider 720 along the rail using power transmitted from the motor 730 driven by the pump control unit 710, and thereby the slider 720 moves along the slide direction of the plunger 762, and the pressure of the fluid in the fluid accommodation portion 765 increases.

Figure 3:
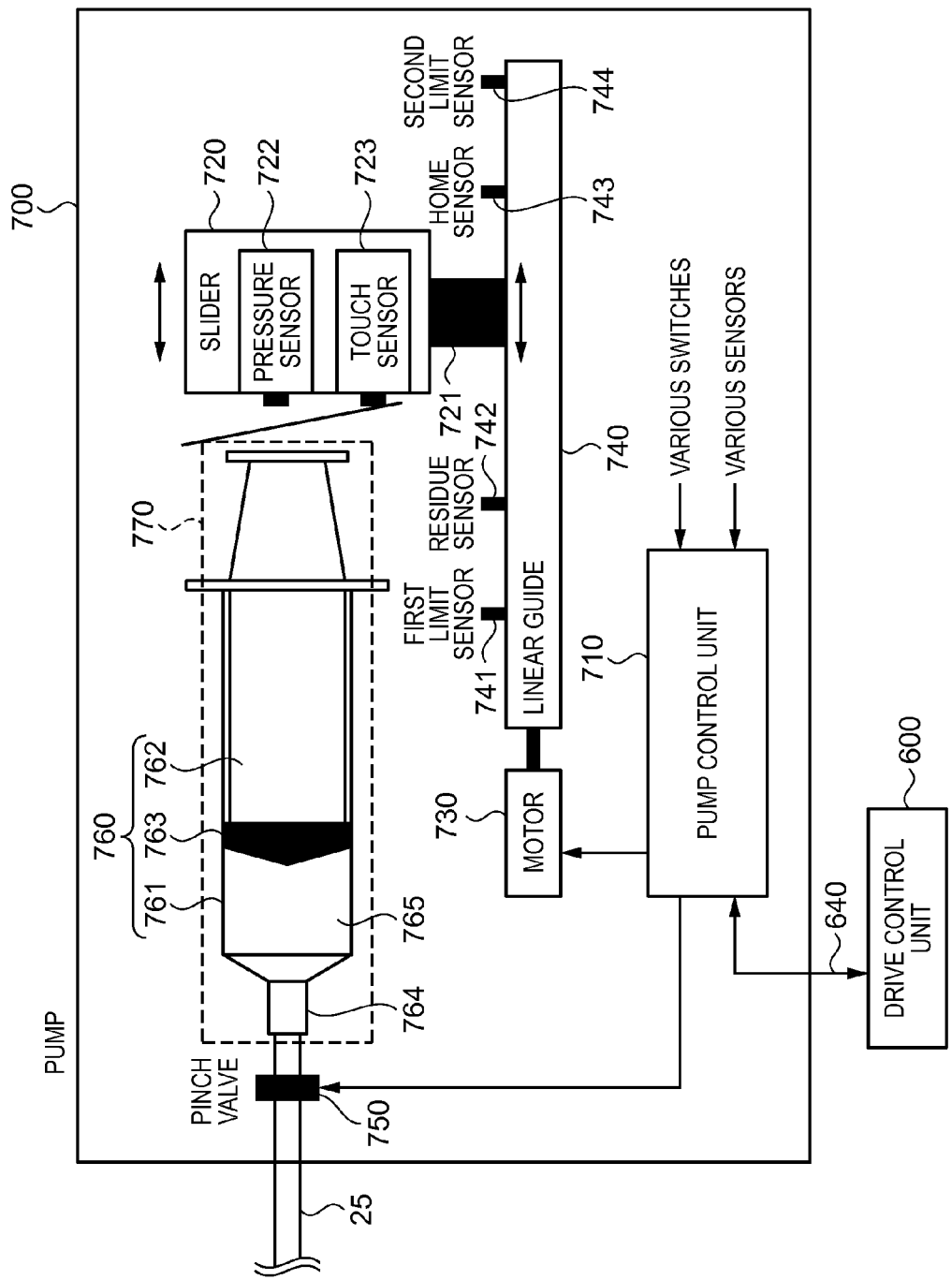
FIG. 3 is a block diagram illustrating the configuration of a pump according to the embodiment of the invention.

As illustrated in FIG. 3, the following sensors are provided along the rail of the linear guide 740: a first limit sensor 741; a residue sensor 742; a home sensor 743; and a second limit sensor 744.

All of the first limit sensor 741, the residue sensor 742, the home sensor 743, and the second limit sensor 744 are sensors for detecting the position of the slider 720 that moves on the rail of the linear guide 740, and signals detected by these sensors are input to the pump control unit 710.

The home sensor 743 is a sensor used to determine an initial position (hereinafter, also referred to as a home position) of the slider 720 on the linear guide 740. The home position is a position in which the slider 720 is held when the fluid container 760 is mounted or replaced.

The residue sensor 742 is a sensor for detecting the position (hereinafter, also referred to as a residual position) of the slider 720 when the residue of the fluid in the fluid container 760 is less than or equal to a predetermined value while the slider 720 moves from the home position in the push-in direction of the plunger 762. When the slider 720 reaches the residual position in which the residue sensor 742 is provided, a predetermined alarm is output to an operator (a practitioner or an assistant). The fluid container 760 currently in use is replaced with a new fluid container 760 at an appropriate time determined by the operator. Alternatively, when an auxiliary second pump 700b having the same configuration as that of the pump 700 (the first pump 700a) is prepared, a switching operation is performed so as to supply the fluid from the auxiliary second pump 700b to the fluid ejection unit 100.

The first limit sensor 741 indicates a limit position (hereinafter, referred to as a first limit position) in a movable range in which the slider 720 can move from the home position in the push-in direction of the plunger 762. When the slider 720 reaches the first limit position in which the first limit sensor 741 is provided, the residue of the fluid in the fluid container 760 is much less than the residue indicating that the slider 720 is present at the residual position, and a predetermined alarm is output to the operator. In this case, the fluid container 760 currently in use is also replaced with a new fluid container 760, or a switching operation is also performed so as to supply the fluid from an auxiliary second pump 700b.

In contrast, the second limit sensor 744 indicates a limit position (hereinafter, also referred to as a second limit position) in a movable range in which the slider 720 can move from the home position in the opposite direction of the push-in direction of the plunger 762. When the slider 720 reaches the second limit position in which the second limit sensor 744 is provided, a predetermined alarm is output.

A touch sensor 723 and a pressure sensor 722 are mounted on the slider 720.

The touch sensor 723 is a sensor for detecting whether the slider 720 is in contact with the plunger 762 of the fluid container 760.

The pressure sensor 722 is a sensor that detects the pressure of the fluid in the fluid accommodation portion 765 formed by the inner wall of the syringe 761 and the gasket 763, and outputs signals in response to a detected pressure.

When the pinch valve 750 is closed, and the slider 720 moves in the push-in direction, and after the slider 720 comes into contact with the plunger 762, the pressure of the fluid in the fluid accommodation portion 765 increases to the extent that the slider 720 moves further in the push-in direction.

In contrast, when the pinch valve 750 is opened, and the slider 720 moves in the push-in direction, and even after the slider 720 comes into contact with the plunger 762, the fluid in the fluid accommodation portion 765 flows out of the nozzle 211 of the fluid ejection unit 100 via the connection tube 25, and thereby the pressure of the fluid in the fluid accommodation portion 765 increases to a certain level, but the pressure of the fluid does not increase even though the slider 720 moves further in the push-in direction.

The touch sensor 723 and the pressure sensor 722 input signals to the pump control unit 710.

A description to be given hereinafter is regarding a preparation operation configured to include a process of mounting a new fluid container 760 filled with the fluid on the fluid container mounting unit 770; a process of supplying the fluid in the fluid container 760 to the fluid ejection unit 100; and a process of bringing the fluid ejection device 1 into a state in which the fluid ejection unit 100 can eject the fluid in a pulsed manner.

First, the operator inputs an ON signal of the slider release switch 780 to the pump control unit 710 by operating the slider release switch 780. Thus, the pump control unit 710 moves the slider 720 to the home position.

The operator mounts the fluid container 760 connected to the connection tube 25 in advance on the fluid container mounting unit 770. The syringe 761 of the fluid container 760 is already filled with the fluid.

When the operator sets the connection tube 25 to the pinch valve 750, and then inputs an ON signal of the pinch valve switch 785 to the pump control unit 710 by operating the pinch valve switch 785, the pump control unit 710 closes the pinch valve 750.

Subsequently, the operator inputs an ON signal of the slider set switch 781 to the pump control unit 710 by operating the slider set switch 781. Thus, the pump control unit 710 starts a control operation in such a manner that the slider 720 moves in the push-in direction and the pressure of the fluid accommodated in the fluid accommodation portion 765 of the fluid container 760 reaches a predetermined target pressure value.

Figure 4:
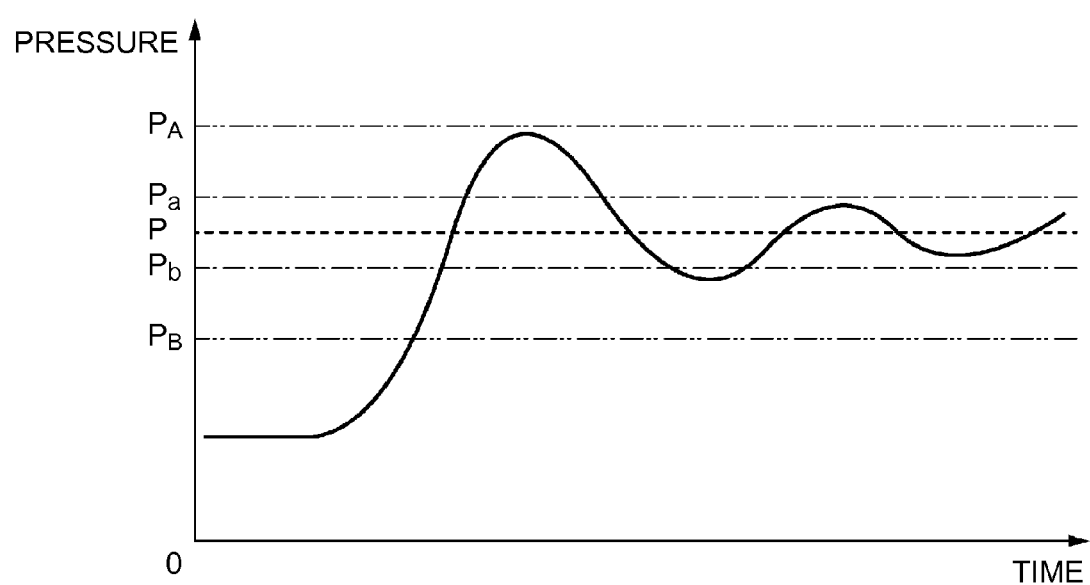
FIG. 4 is a graph illustrating a change in the pressure of a fluid in a fluid accommodation portion according to the embodiment of the invention.

FIG. 4 is a graph illustrating a change in the inner fluid pressure of the fluid accommodation portion 765.

When the target pressure value is P, preferably, a second upper limit pressure value $P_a$ is set to be higher than P, a second lower limit pressure value $P_b$ is set to be lower than P, the pump control unit 710 controls the inner fluid pressure of the fluid accommodation portion 765 to be in a second pressure range (hereinafter, also referred to as a fine window) of from $P_a$ to $P_b$, and a center value of the fine window is the target pressure value P.

Thereafter, when the operator inputs an ON signal of the fluid supply ready switch 782 to the pump control unit 710 by pushing the fluid supply ready switch 782, and the pressure of the fluid in the fluid accommodation portion 765 enters a specific range (hereinafter, also referred to as a rough window) for the target pressure value, the pump control unit 710 is brought into a fluid suppliable state in which the fluid is allowed to be supplied from the pump 700 to the fluid ejection unit 100. When a first upper limit pressure value $P_A$ is set to be higher than the second upper limit pressure value $P_a$, and a first lower limit pressure value $P_B$ is set to be lower than the second lower limit pressure value $P_b$, the rough window refers to a first pressure range of from $P_A$ to $P_B$, and a center value of the rough window is the target pressure value P.

In a state where the pump control unit 710 can supply the fluid, when the operator inputs a fluid supply signal of the priming switch 783 to the pump control unit 710 by operating the priming switch 783, the pump control unit 710 starts a priming process. The priming process is a process by which a fluid channel from the fluid container 760 to the connection tube 25 and to a fluid ejection opening 212 of the fluid ejection unit 100 is filled up with the fluid.

When the priming process starts, the pump control unit 710 opens the pinch valve 750, and starts moving the slider 720 in the push-in direction at the same time or substantially the same time (for example, a time gap of approximately several milliseconds or approximately several tens of milliseconds) as when the pinch valve 750 is opened, or at a time when the pinch valve 750 is opened. The slider 720 moves at a predetermined speed in such a manner that a constant amount of the fluid per unit time is supplied from the fluid container 760. The priming process is performed until a predetermined amount of time required to complete the priming process has elapsed (or the slider 720 moves by a predetermined distance), or the operator inputs an OFF signal of the priming switch 783 by operating the priming switch 783.

Accordingly, a predetermined amount of the fluid in the fluid accommodation portion 765 is supplied at a predetermined flow speed (the amount of discharge of the fluid per unit time) from the pump 700, the connection tube 25 from the pinch valve 750 to the fluid ejection unit 100 is filled up with the fluid, and the fluid chamber 501 of the fluid ejection unit 100, the fluid ejection tube 200 and the like are filled up with the fluid. Air present in the connection tube 25 or the fluid ejection unit 100 prior to the starting of the priming process is released to the atmosphere via the nozzle 211 of the fluid ejection unit 100 as the fluid flows into the connection tube 25 or the fluid ejection unit 100.

The pump control unit 710 pre-stores the predetermined speed, the predetermined distance, and the predetermined amount of time in relation to the movement of the slider 720 during the priming process.

As such, the priming process is completed.

Subsequently, when the operator inputs an ejection signal of the flushing switch 628 to the drive control unit 600 by operating the flushing switch 628, the drive control unit 600 starts a deaeration process. The deaeration process is a process by which air bubbles remaining in the connection tube 25 or the fluid ejection unit 100 are discharged via the nozzle 211 of the fluid ejection unit 100.

In the deaeration process, in a state in which the pinch valve 750 is opened, the pump control unit 710 moves the slider 720 in the push-in direction at the predetermined speed in such a manner that a constant amount of the fluid per unit time is supplied from the fluid container 760, and the fluid is supplied to the fluid ejection unit 100. The drive control unit 600 drives the piezoelectric element 401 of the fluid ejection unit 100 in conjunction with the discharge of the fluid by the pump 700, and thereby the fluid is ejected from the fluid ejection unit 100. Accordingly, air bubbles remaining in the connection tube 25 or the fluid ejection unit 100 are discharged via the nozzle 211 of the fluid ejection unit 100. The deaeration process is performed until a predetermined amount of time has elapsed (or the slider 720 moves by a predetermined distance), or the operator inputs an OFF signal of the flushing switch 628 by operating the flushing switch 628.

When the deaeration process is completed, the pump control unit 710 closes the pinch valve 750, and detects the pressure of the fluid accommodated in the fluid accommodation portion 765 of the fluid container 760. The pump control unit 710 performs a control operation of adjusting the position of the slider 720 in such a manner that the pressure reaches the target pressure value.

Thereafter, when the pressure of the fluid in the fluid accommodation portion 765 enters the specific range (the rough window) for the target pressure value, the fluid can be ejected from the fluid ejection unit 100 in a pulsed manner.

In this state, when the operator inputs a fluid supply signal from the fluid ejection unit start-up switch 625 to the drive control unit 600 by operating the fluid ejection unit start-up switch 625, the pump control unit 710 opens the pinch valve 750 in response to the signal transmitted from the drive control unit 600, and after the pinch valve 750 is opened, the pump control unit 710 starts the supply of the fluid to the fluid ejection unit 100 by moving the slider 720 at a predetermined speed in the push-in direction. In contrast, the drive control unit 600 generates a pulsed flow by starting the driving of the piezoelectric element 401 and changing the volume of the fluid chamber 501. Accordingly, the fluid is ejected in a pulsed manner at a high speed via the nozzle 211 at the tip of the fluid ejection unit 100.

Thereafter, when the operator inputs an OFF signal of the fluid ejection unit start-up switch 625 to the drive control unit 600 by operating the fluid ejection unit start-up switch 625, the drive control unit 600 stops the driving of the piezoelectric element 401. The pump control unit 710 stops the movement of the slider 720 in response to signals transmitted from the drive control unit 600, and closes the pinch valve 750. As such, the fluid ejection unit 100 stops the ejection of the fluid.

Figure 5:
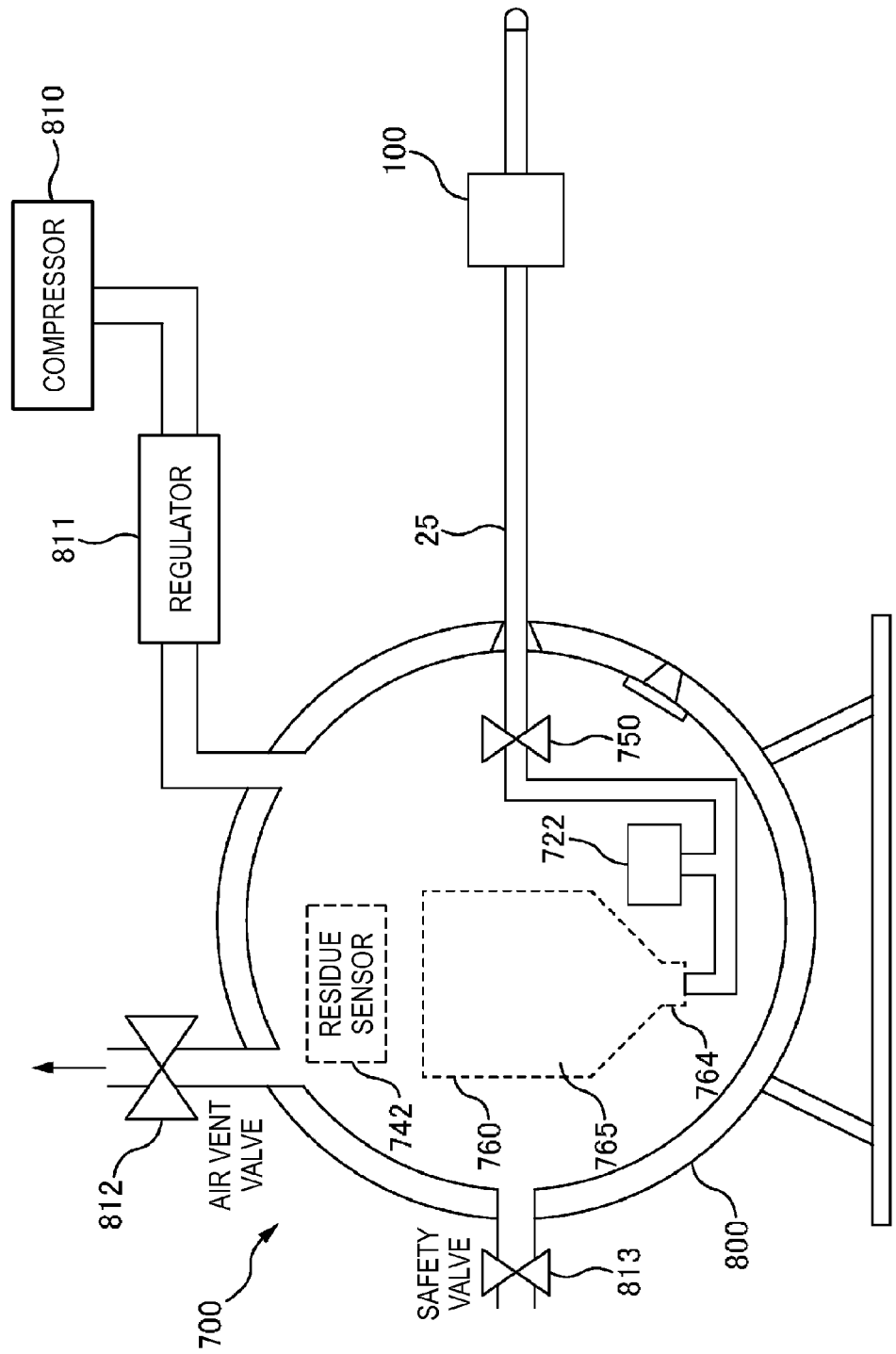
FIG. 5 is a block diagram illustrating another example of the configuration of the pump according to the embodiment of the invention.

The pump 700 according to the embodiment is configured such that the slider 720 presses the fluid container 760 which is formed of a medical syringe configured to include the syringe 761 and the plunger 762; however, the pump 700 may be configured as illustrated in FIG. 5.

The pump 700 illustrated in FIG. 5 has the following configuration: the fluid container 760 (an infusion solution bag that accommodates a fluid) is mounted in a pressurized chamber 800, and after air supplied from a compressor 810 is regulated by a regulator 811, the air is pressure-fed into the pressurized chamber 800, and thereby the fluid container 760 is pressed.

When the pinch valve 750 is opened in a state where the fluid container 760 is pressed by the pressurization of air in the pressurized chamber 800, the fluid accommodated in the fluid accommodation portion 765 of the fluid container 760 flows out of the opening 764, and is supplied to the fluid ejection unit 100 via the connection tube 25.

The air in the pressurized chamber 800 is released to the atmosphere by the opening of an air vent valve 812. In a case where the pressure of the air in the pressurized chamber 800 exceeds a predetermined pressure, even when the air vent valve 812 is not opened, a safety valve 813 is opened, and thereby the air in the pressurized chamber 800 is released to the atmosphere.

The pump control unit 710 controls the compressor 810; the regulator 811; the air vent valve 812; and the pinch valve 750, the control scheme of which is not illustrated in FIG. 5.

The following sensors input detected output signals to the pump control unit 710: the pressure sensor 722 that detects the pressure of the fluid in the fluid container 760, and the residue sensor 742 that detects the residue of the fluid in the fluid container 760.

When the pump 700 with this configuration is adopted, it is possible to increase the amount of the fluid which can be supplied to the fluid ejection unit 100 per unit time. Since the fluid ejection unit 100 can supply the fluid at a high pressure, and an infusion solution bag that accommodates the fluid is used as the fluid container 760 as it is, it is possible to prevent the fluid from being contaminated. The fluid ejection unit 100 can continuously supply the fluid without generating pulsation.

In addition, in the embodiment, the drive control unit 600 is provided separately from the pump 700 and the fluid ejection unit 100; however, the drive control unit 600 may be provided integrally with the pump 700.

When the practitioner performs an operation using the fluid ejection device 1, the practitioner grasps the fluid ejection unit 100. Accordingly, the connection tube 25 up to the fluid ejection unit 100 is preferably as flexible as possible. For this reason, a flexible thin tube is used as the connection tube 25, and a fluid discharge pressure of the pump 700 is preferably set to a low pressure in a pressure range in which the fluid can be supplied to the fluid ejection unit 100. For this reason, the discharge pressure of the pump 700 is set to approximately 0.3 atm (0.03 MPa) or less.

In particular, in a case where a malfunction of an apparatus may lead to a serious accident, for example, for a brain surgery, it is necessary to prevent the cutting of the connection tube 25 from causing the ejection of the fluid at a high pressure, and also, for this reason, the discharge pressure of the pump 700 is required to be set to a low pressure.

Fluid Ejection Unit

Subsequently, the structure of the fluid ejection unit 100 according to the embodiment will be described.

Figure 6:
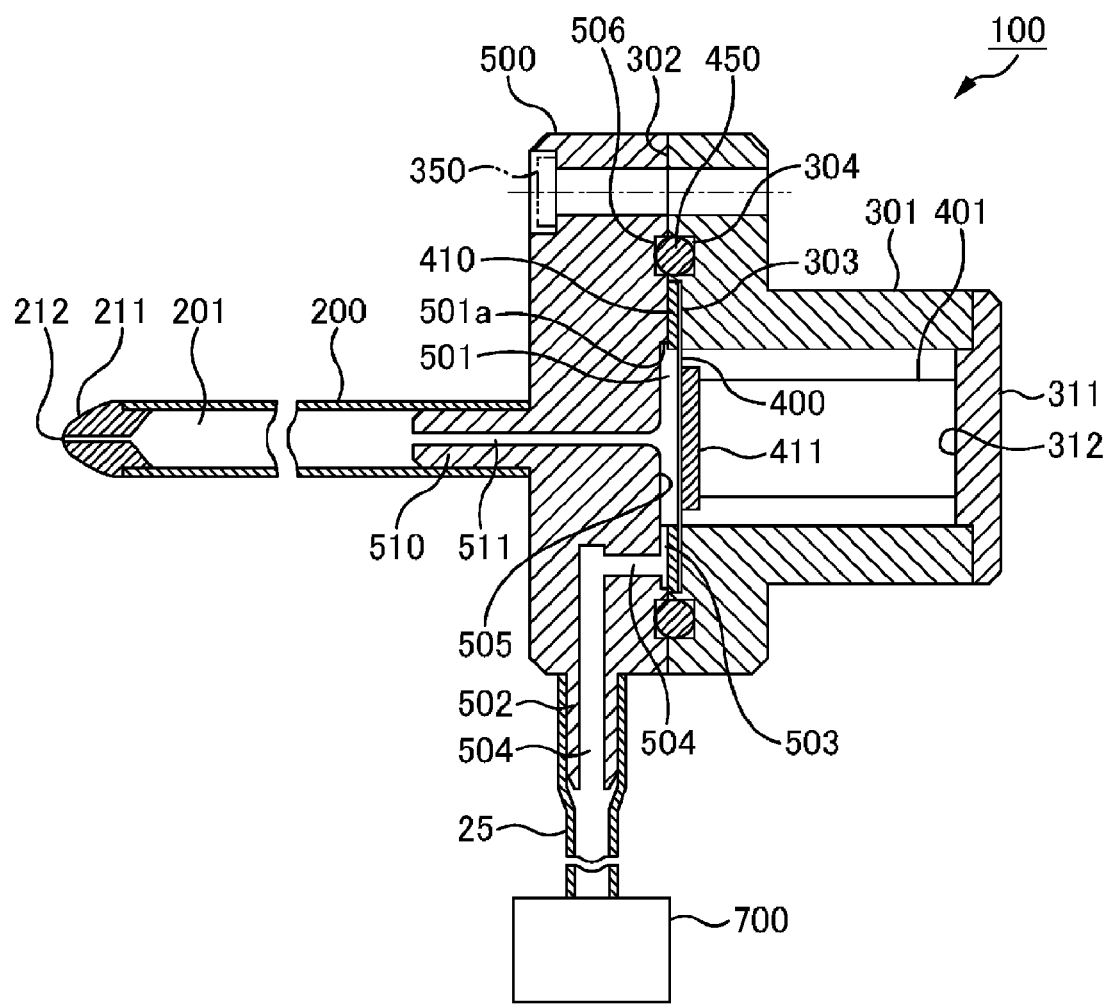
FIG. 6 is a cross-sectional view illustrating the structure of a fluid ejection unit according to the embodiment of the invention.

FIG. 6 is a cross-sectional view illustrating the structure of the fluid ejection unit 100 according to the embodiment. In FIG. 6, the fluid ejection unit 100 includes a pulse generation unit that generates the pulsation of the fluid, and is connected to the fluid ejection tube 200 having an ejection channel 201 as a channel through which the fluid is discharged.

In the fluid ejection unit 100, an upper case 500 and a lower case 301 are screwed together with four fixation screws 350 (not illustrated) while the respective facing surfaces thereof are bonded to each other. The lower case 301 is a cylindrical member having a flange, and one end portion of the lower case 301 is sealed with a bottom plate 311. The piezoelectric element 401 is provided in an inner space of the lower case 301.

The piezoelectric element 401 is a stack-type piezoelectric element, and acts as an actuator. One end portion of the piezoelectric element 401 is firmly fixed to the diaphragm 400 via an upper plate 411, and the other end portion is firmly fixed to an upper surface 312 of the bottom plate 311.

The diaphragm 400 is made of a circular disc-like thin metal plate, and a circumferential edge portion of the diaphragm 400 is firmly fixed to a bottom surface of a concave portion 303 in the lower case 301 while being in close contact with the bottom surface of the concave portion 303. When an ejection signal is input to the piezoelectric element 401 that acts as a volume varying unit, the piezoelectric element 401 changes the volume of the fluid chamber 501 via the diaphragm 400 through the extension and contraction thereof. A reinforcement plate 410 is provided in such a manner as to be stacked on an upper surface of the diaphragm 400, and is made of a circular disc-like thin metal plate having an opening at the center thereof.

The upper case 500 has a concave portion formed in a center portion of the surface facing the lower case 301, and the fluid chamber 501 is a rotator-shaped space formed by this concave portion and the diaphragm 400 and filled with the fluid. That is, the fluid chamber 501 is a space enveloped by a sealing surface 505 and an inner circumferential side wall 501a of the concave portion of the upper case 500, and the diaphragm 400. An outlet channel 511 is drilled in an approximately center portion of the fluid chamber 501.

The outlet channel 511 passes through the outlet channel tube 510 from the fluid chamber 501 to an end portion of an outlet channel tube 510 provided in such a manner as to protrude from one end surface of the upper case 500. A connection portion between the outlet channel 511 and the sealing surface 505 of the fluid chamber 501 is smoothly rounded so as to reduce fluid resistance.

In the embodiment (refer to FIG. 6), the fluid chamber 501 has a substantially cylindrical shape having sealed opposite ends; however, the fluid chamber 501 may have a conical shape, a trapezoidal shape, a hemispherical shape, or the like in a side view, and the shape of the fluid chamber 501 is not limited to a cylindrical shape. For example, when the connection portion between the outlet channel 511 and the sealing surface 505 has a funnel shape, air bubbles in the fluid chamber 501 (to be described later) are easily discharged.

The fluid ejection tube 200 is connected to the outlet channel tube 510. The ejection channel 201 is drilled in the fluid ejection tube 200, and the diameter of the ejection channel 201 is larger than that of the outlet channel 511. In addition, the tube thickness of the fluid ejection tube 200 is formed so as to have a range of rigidity in which the fluid ejection tube 200 does not absorb pressure pulsation of the fluid.

The nozzle 211 is inserted into the tip end portion of the fluid ejection tube 200. A fluid ejection opening 212 is drilled in the nozzle 211. The diameter of the fluid ejection opening 212 is smaller than that of the ejection channel 201.

An inlet channel tube 502 is provided in such a manner as to protrude from a side surface of the upper case 500, and is inserted into the connection tube 25 through which the fluid is supplied from the pump 700. A channel 504 for the inlet channel is drilled in the inlet channel tube 502. The channel 504 communicates with an inlet channel 503. The inlet channel 503 is formed in a groove shape in a circumferential edge portion of the sealing surface 505 of the fluid chamber 501, and communicates with the fluid chamber 501.

A packing box 304 and a packing box 506 are respectively formed in the bonded surfaces of the lower case 301 and the upper case 500 at positions separated from an outer circumferential direction of the diaphragm 400, and a ring-shaped packing 450 is mounted in a space formed by the packing boxes 304 and 506.

Here, when the upper case 500 and the lower case 301 are assembled together, the circumferential edge portion of the diaphragm 400 is in close contact with a circumferential edge portion of the reinforcement plate 410 due to the circumferential edge portion of the sealing surface 505 of the upper case 500 and the bottom surface of the concave portion 303 of the lower case 301. At this time, the packing 450 is pressed by the upper case 500 and the lowercase 301, and thereby the fluid is prevented from leaking from the fluid chamber 501.

Since the inner pressure of the fluid chamber 501 becomes a high pressure of 30 atm (3 MPa) or greater during the discharge of the fluid, the fluid may slightly leak from the respective connections between the diaphragm 400, the reinforcement plate 410, the upper case 500, and the lower case 301; however, the leakage of the fluid is prevented due to the packing 450.

As illustrated in FIG. 6, in the case where the packing 450 is provided, since the packing 450 is compressed due to the pressure of the fluid leaking from the fluid chamber 501 at a high pressure, and is strongly pressed against the respective walls of the packing boxes 304 and 506, it is possible to more reliably prevent the leakage of the fluid. For this reason, it is possible to maintain a considerable increase in the inner pressure of the fluid chamber 501 during the driving of the fluid ejection unit 100.

Subsequently, the inlet channel 503 formed in the upper case 500 will be described with reference to the drawings in more detail.

Figure 7:
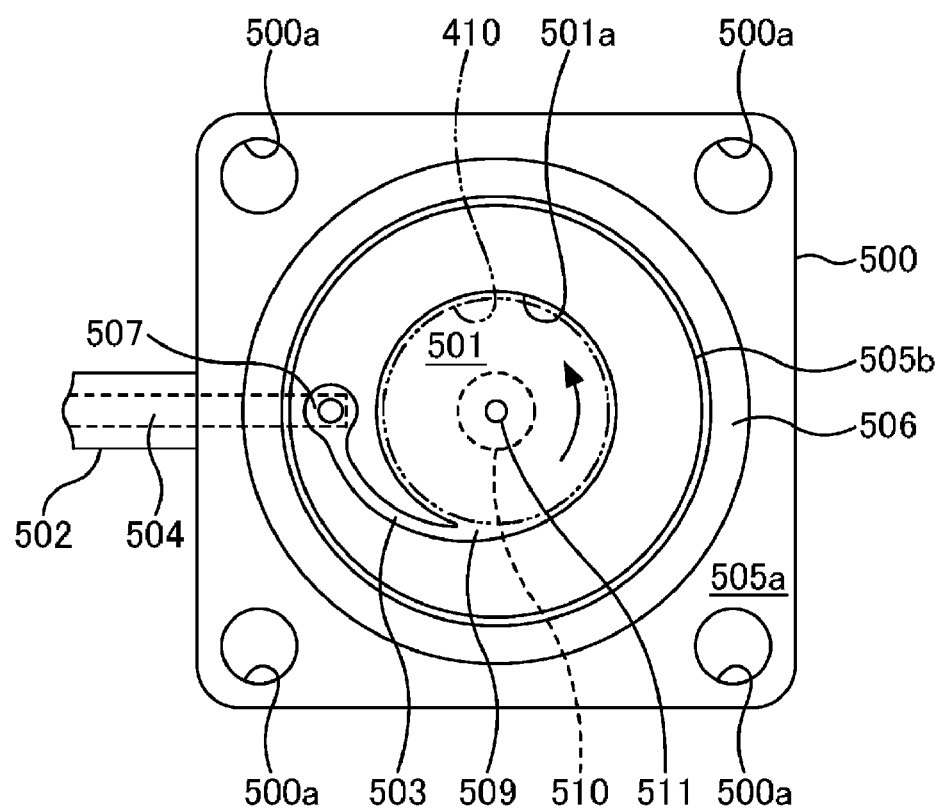
FIG. 7 is a plan view illustrating the shape of an inlet channel according to the embodiment of the invention.

FIG. 7 is a plan view illustrating the shape of the inlet channel 503, and FIG. 7 illustrates the shape of the upper case 500 when the surface of the upper case 500 bonded to the lower case 301 is seen. In FIG. 7, the inlet channel 503 is formed in a groove shape in the circumferential edge portion of the sealing surface 505 of the upper case 500.

One end portion of the inlet channel 503 communicates with the fluid chamber 501, and the other end portion communicates with the channel 504. A fluid sump 507 is formed in a connection portion between the inlet channel 503 and the channel 504. A connection portion between the fluid sump 507 and the inlet channel 503 is smoothly rounded, and thereby fluid resistance is reduced.

The inlet channel 503 communicates with the fluid chamber 501 in a substantially tangential direction with respect to an inner circumferential side wall 501a of the fluid chamber 501. The fluid supplied from the pump 700 (refer to FIG. 1) at a predetermined pressure flows along the inner circumferential side wall 501a (in a direction illustrated by the arrow in FIG. 7), and generates a swirl flow in the fluid chamber 501. The swirl flow is pushed against the inner circumferential side wall 501a due to a centrifugal force associated with the swirling of the fluid, and air bubbles in the fluid chamber 501 are concentrated in a center portion of the swirl flow.

The air bubbles concentrated in the center portion are discharged via the outlet channel 511. For this reason, the outlet channel 511 is preferably provided in the vicinity of the center of the swirl flow, that is, in an axial center portion of a rotor shape.

As illustrated in FIG. 7, the inlet channel 503 is curved. The inlet channel 503 may communicate with the fluid chamber 501 while not being curved but being linearly formed; however, when the inlet channel 503 is curved, a channel length is increased, and a desired inertance (to be described later) is obtained in a small space.

As illustrated in FIG. 7, the reinforcement plate 410 is provided between the diaphragm 400 and the circumferential edge portion of the sealing surface 505, in which the inlet channel 503 is formed. The reinforcement plate 410 is provided so as to improve the durability of the diaphragm 400. Since a cut-out connection opening 509 is formed in a connection portion between the inlet channel 503 and the fluid chamber 501, when the diaphragm 400 is driven at a high frequency, stress may be concentrated in the vicinity of the connection opening 509, and thereby a fatigue failure may occur in the vicinity of the connection opening 509. It is possible to prevent stress from being concentrated on the diaphragm 400 by providing the reinforcement plate 410 with an opening not having a cut-out portion and being continuously formed.

Four screw holes 500a are respectively provided in outer circumferential corner portions of the upper case 500, and the upper case 500 and the lower case 301 are bonded to each other via screwing at the positions of the screw holes.

It is possible to firmly fix the reinforcement plate 410 and the diaphragm 400 in an integrally stacked state by bonding together the reinforcement plate 410 and the diaphragm 400, which is not illustrated. An adhesive method using an adhesive, a solid-state diffusion bonding method, a welding method, or the like may be used so as to firmly fix together the reinforcement plate 410 and the diaphragm 400; however, the respective bonded surfaces of the reinforcement plate 410 and the diaphragm 400 are preferably in close contact with each other.

Operation of Fluid Ejection Unit

Subsequently, an operation of the fluid ejection unit 100 according to the embodiment will be described with reference to FIGS. 1 to 7. The fluid ejection unit 100 according to the embodiment discharges the fluid due to a difference between an inertance L1 (may be referred to as a combined inertance L1) of the inlet channel 503 and the peripherals and an inertance L2 (may be referred to as a combined inertance L2) of the outlet channel 511 and the peripherals.

Inertance

First, the inertance will be described.

An inertance L is expressed by $L=\rho \times h/S$, and here, $\rho$ is the density of a fluid, S is the cross-sectional area of a channel, and h is a channel length. When $\Delta P$ is a differential pressure of the channel, and Q is a flow rate of the fluid flowing through the channel, it is possible to deduce a relationship $\Delta P = L \times dQ/dt$ by modifying an equation of motion in the channel using the inertance L.

That is, the inertance L indicates a degree of influence on a change in flow rate with time, and a change in flow rate with time decreases to the extent that the inertance L is large, and a change in flow rate with time increases to the extent that the inertance L is small.

Similar to a parallel connection or a series connection of inductances in an electric circuit, it is possible to calculate a combined inertance with respect to a parallel connection of a plurality of channels or a series connection of a plurality of channels having different shapes by combining an inertance of each of the channels.

Since the diameter of the channel 504 is set to be larger much than that of the inlet channel 503, the inertance L1 of the inlet channel 503 and the peripherals can be calculated from a boundary of the inlet channel 503. At this time, since the connection tube 25 that connects the pump 700 and the inlet channel 503 is flexible, the connection tube 25 may not be taken into consideration in calculating the inertance L1.

Since the diameter of the ejection channel 201 is larger much than that of the outlet channel 511, and the tube (tube wall) thickness of the fluid ejection tube 200 is thin, the inertance L2 of the outlet channel 511 and the peripherals has a negligible influence on the inertance L2. Accordingly, the inertance L2 of the outlet channel 511 and the peripherals may be replaced with an inertance of the outlet channel 511. The rigidity of the tube wall thickness of the fluid ejection tube 200 is sufficient to propagate the pressure of the fluid.

In the embodiment, a channel length and a cross-sectional area of the inlet channel 503 and a channel length and a cross-sectional area of the outlet channel 511 are set in such a manner that the inertance L1 of the inlet channel 503 and the peripherals is greater than the inertance L2 of the outlet channel 511 and the peripherals.

Ejection of Fluid

Subsequently, an operation of the fluid ejection unit 100 will be described.

The pump 700 supplies the fluid to the inlet channel 503 at a predetermined pressure. As a result, when the piezoelectric element 401 is not operated, the fluid flows into the fluid chamber 501 due to a difference between a discharge force of the pump 700 and a fluid resistance value for the entirety of the inlet channel 503 and the peripherals.

Here, in a case where the inertance L1 of the inlet channel 503 and the peripherals and the inertance L2 of the outlet channel 511 and the peripherals are considerably large, when an ejection signal is input to the piezoelectric element 401, and the piezoelectric element 401 extends rapidly, the inner pressure of the fluid chamber 501 increases rapidly, and reaches several tens of atmosphere.

Since the inner pressure of the fluid chamber 501 is larger much than the pressure applied to the inlet channel 503 by the pump 700, the flow of the fluid from the inlet channel 503 to the fluid chamber 501 decreases due to the pressure, and the flow of the fluid out of the outlet channel 511 increases.

Since the inertance L1 of the inlet channel 503 is larger than the inertance L2 of the outlet channel 511, an increase in a flow rate of the fluid discharged from the outlet channel 511 is larger than a decrease in a flow rate of the fluid flowing from the inlet channel 503 into the fluid chamber 501. Accordingly, the fluid is discharged in a pulsed manner to the ejection channel 201, that is, a pulsed flow occurs. Discharge pressure pulsation propagates in the fluid ejection tube 200, and the fluid is ejected via the fluid ejection opening 212 of the nozzle 211 at the tip end.

Here, since the diameter of the fluid ejection opening 212 of the nozzle 211 is smaller than that of the outlet channel 511, a pulsed flow of the fluid is ejected as droplets at a higher pressure and speed.

In contrast, immediately after a pressure increase, the inner pressure of the fluid chamber 501 becomes negative due to interaction between a decrease in the amount of inflow of the fluid from the inlet channel 503 and an increase in the amount of outflow of the fluid from the outlet channel 511. As a result, after a predetermined amount of time has elapsed, due to both of the pressure of the pump 700 and the negative inner pressure of the fluid chamber 501, the fluid flows from the inlet channel 503 into the fluid chamber 501 again at the same speed as that before the operation of the piezoelectric element 401.

When the piezoelectric element 401 extends after the flow of the fluid in the inlet channel 503 is restored, it is possible to continuously eject the fluid in the form of a pulsed flow via the nozzle 211.

Discharge of Air Bubbles

Subsequently, an operation of discharging air bubbles from the fluid chamber 501 will be described.

As described above, the inlet channel 503 communicates with the fluid chamber 501 via a path that approaches the fluid chamber 501 while swirling around the fluid chamber 501. The outlet channel 511 is provide in the vicinity of a rotational axis of a substantially rotor-shaped fluid chamber 501.

For this reason, the fluid flowing from the inlet channel 503 into the fluid chamber 501 swirls along the inner circumferential side wall 501a of the fluid chamber 501. The fluid is pushed against the inner circumferential side wall 501a of the fluid chamber 501 due to a centrifugal force, and air bubbles contained in the fluid are concentrated in the center portion of the fluid chamber 501, and are discharged via the outlet channel 511.

Accordingly, even when a small amount of the volume of the fluid chamber 501 is changed in association with the operation of the piezoelectric element 401, it is possible to obtain a sufficient pressure increase while a pressure pulsation is not adversely affected by the air bubbles.

In the embodiment, since the pump 700 supplies the fluid to the inlet channel 503 at a predetermined pressure, even when the driving of the fluid ejection unit 100 is stopped, the fluid is supplied to the inlet channel 503 and the fluid chamber 501. Accordingly, it is possible to start an initial operation without an aid of a prime operation.

Since the fluid is ejected via the fluid ejection opening 212 having a diameter smaller than that of the outlet channel 511, an inner fluid pressure is increased higher than that of the outlet channel 511, and thereby it is possible to eject the fluid at a high speed.

Since the rigidity of the fluid ejection tube 200 is sufficient to transmit a pulsation of the fluid from the fluid chamber 501 to the fluid ejection opening 212, it is possible to eject a desired pulsed fluid without disturbing pressure propagation of the fluid from the fluid ejection unit 100.

Since the inertance of the inlet channel 503 is set to be larger than that of the outlet channel 511, an increase in the amount of outflow of the fluid from the outlet channel 511 is larger than a decrease in the amount of inflow of the fluid from the inlet channel 503 into the fluid chamber 501, and it is possible to discharge the fluid into the fluid ejection tube 200 in the form of a pulsed flow. Accordingly, a check valve is not required to be provided in the inlet channel 503, it is possible to simplify the structure of the fluid ejection unit 100, it is easy to clean the inside of the fluid ejection unit 100, and it is possible to remove a potential durability problem associated with the use of the check valve.

Since the respective inertances of both of the inlet channel 503 and the outlet channel 511 are set to be considerably large, it is possible to rapidly increase the inner pressure of the fluid chamber 501 by rapidly reducing the volume of the fluid chamber 501.

Since the piezoelectric element 401 as a volume varying unit and the diaphragm 400 are configured to generate a pulsation, it is possible to simplify the structure of the fluid ejection unit 100, and to reduce the size of the fluid ejection unit 100 in association therewith. It is possible to set the maximum frequency of a change in the volume of the fluid chamber 501 to a high frequency of 1 KHz or greater, and the fluid ejection unit 100 is optimized to eject a pulsed flow of the fluid at a high speed.

In the fluid ejection unit 100, since the inlet channel 503 generates a swirl flow of the fluid in the fluid chamber 501, the fluid in the fluid chamber 501 is pushed in an outer circumferential direction of the fluid chamber 501 due to a centrifugal force, air bubbles contained in the fluid are concentrated in the center portion of the swirl flow, that is, in the vicinity of the axis of the substantially rotor shape, and thereby it is possible to discharge the air bubbles via the outlet channel 511 provided in the vicinity of the axis of the substantially rotor shape. For this reason, it is possible to prevent a decrease in pressure amplitude associated with the stagnation of air bubbles in the fluid chamber 501, and it is possible to continuously and stably drive the fluid ejection unit 100.

Since the inlet channel 503 is formed in such a manner as to communicate with the fluid chamber 501 via the path that approaches the fluid chamber 501 while swirling around the fluid chamber 501, it is possible to generate a swirl flow without adopting a structure dedicated for swirling the fluid in the fluid chamber 501.

Since the groove-shaped inlet channel 503 is formed in the outer circumferential edge portion of the sealing surface 505 of the fluid chamber 501, it is possible to form the inlet channel 503 (a swirl flow generation unit) without increasing the number of components.

Since the reinforcement plate 410 is provided on the upper surface of the diaphragm 400, the diaphragm 400 is driven with respect to an outer circumference (a fulcrum) of the opening of the reinforcement plate 410, and thereby the concentration of stress is unlikely to occur, and it is possible to improve the durability of the diaphragm 400.

When corners of the surface of the reinforcement plate 410 bonded to the diaphragm 400 are rounded, it is possible to further reduce the concentration of stress on the diaphragm 400.

When the reinforcement plate 410 and the diaphragm 400 are firmly and integrally fixed together while being stacked on each other, it is possible to improve the assemblability of the fluid ejection unit 100, and it is possible to reinforce the outer circumferential edge portion of the diaphragm 400.

Since the fluid sump 507 for the stagnation of the fluid is provided in the connection portion between the channel 504 on an inlet side for supplying the fluid from the pump 700 and the inlet channel 503, it is possible to prevent the inertance of the channel 504 from affecting the inlet channel 503.

In the respective bonded surfaces of the lower case 301 and the upper case 500, the ring-shaped packing 450 is provided at the position separated from the outer circumferential direction of the diaphragm 400, and thereby it is possible to prevent the leakage of the fluid from the fluid chamber 501, and to prevent a decrease in the inner pressure of the fluid chamber 501.

Control Unit

Subsequently, a control of the drive control unit 600 and the pump control unit 710 according to the embodiment will be described with reference to FIGS. 8 and 9.

As illustrated in FIGS. 1 and 3, in regard to the control unit according to the embodiment, the drive control unit 600 is connected to the fluid ejection unit 100 via the control cable 630, and is connected to the pump control unit 710 via the communication cable 640. The pump control unit 710 is connected to the motor 730 of the pump 700, and the pinch valve 750.

Preparation Operation

Figure 8:
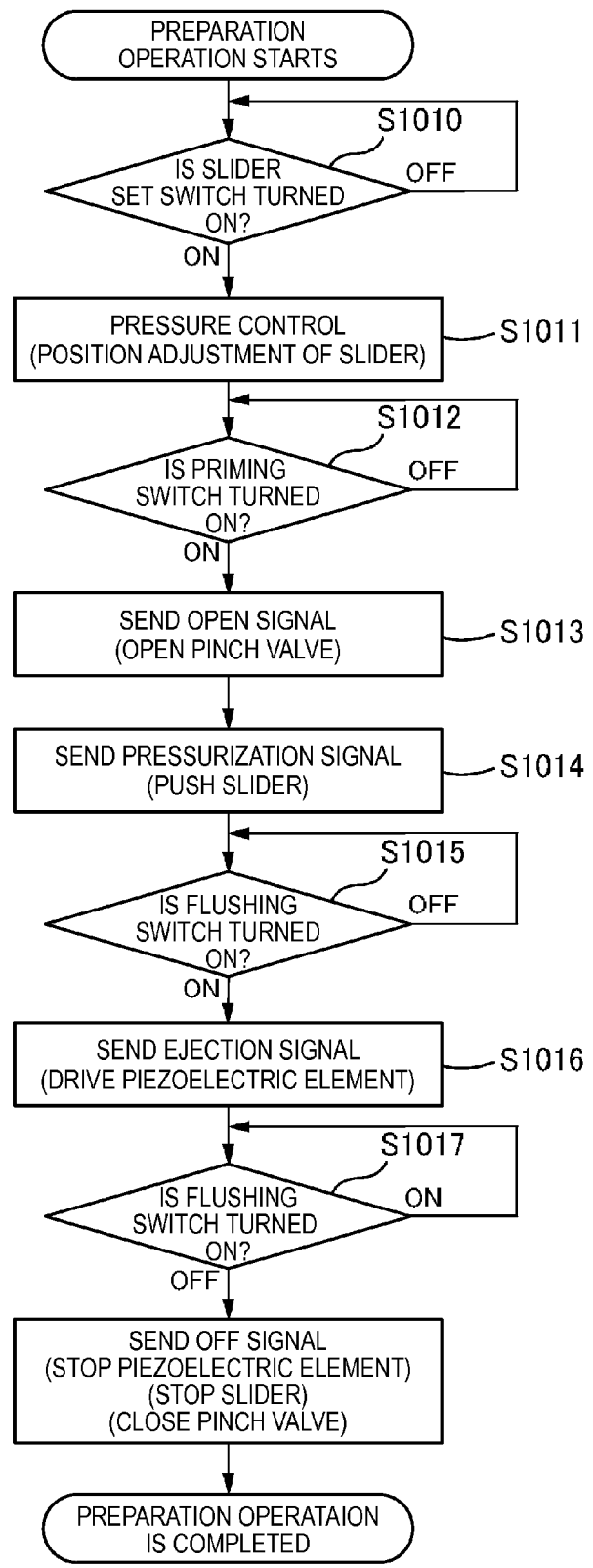
FIG. 8 is a flowchart illustrating a preparation operation of the fluid ejection device according to the embodiment of the invention.

FIG. 8 is a flowchart illustrating a preparation operation of the fluid ejection device according to the embodiment, and the drive control unit 600 and the pump control unit 710 controls the preparation operation of the fluid ejection device 1.

An operator operates the slider release switch 780 in advance, and thereby the pump control unit 710 moves the slider 720 to a home position, and the connection tube 25 is set to the pinch valve 750. In addition, when the operator operates the pinch valve switch 785, the pump control unit 710 closes the pinch valve 750.

First, when the operator turns on the slider set switch 781, the pump control unit 710 receives an ON signal (S1010), and the pump control unit 710 controls the inner fluid pressure of the fluid accommodation portion 765 to become the target pressure value, and a changed pressure value to be in the fine window by moving the slider 720 (S1011).

In the embodiment, when a pressure value of the fluid in the fluid accommodation portion 765 is in the rough window, the fluid can be supplied, and thereby it is possible to start a fluid ejection operation (to be described later). The pump control unit 710 can continuously control the fluid pressure in the rough window to be in the fine window until the fluid is ejected. The inner fluid pressure of the fluid accommodation portion 765 is not controlled during the ejection of the fluid.

In a state where the fluid in the fluid accommodation portion 765 can be supplied, when the operator turns on the priming switch 783, the pump control unit 710 receives a fluid supply signal (S1012), the pump control unit 710 sends an open signal to open the pinch valve 750. (S1013).

The pump control unit 710 sends a pressurization signal at the same time or after the pinch valve 750 is opened, and thereby the slider 720 moves in the push-in direction at the predetermined speed, for the predetermined amount of time, or by the predetermined distance, all of which are pre-stored, and the fluid in the fluid accommodation portion 765 is supplied, and the connection tube 25, the fluid chamber 501 of the fluid ejection unit 100, and the fluid ejection tube 200 are filled up with the fluid (S1014), and air remaining in the connection tube 25 or the fluid ejection unit 100 is discharged.

Thereafter, the flushing process starts due to the turning on of the flushing switch 628 by the operator (S1015).

When the flushing switch 628 is turned on, the drive control unit 600 ejects the fluid from the fluid ejection unit 100 by sending an ejection signal to the fluid ejection unit 100 and driving the piezoelectric element 401 (S1016). Accordingly, air bubbles remaining in the connection tube 25 or the fluid ejection unit 100 are discharged.

When the operator turns off the flushing switch 628, the drive control unit 600 receives an OFF signal (S1017), and the drive control unit 600 stops the driving of the piezoelectric element 401 by sending the OFF signal to the fluid ejection unit 100 and the pump control unit 710, and when the pump control unit 710 receives the signal from the drive control unit 600, the pump control unit 710 stops the slider 720, and closes the pinch valve 750 (S1018). As such, the preparation operation is completed.

Ejection Operation

Figure 9:
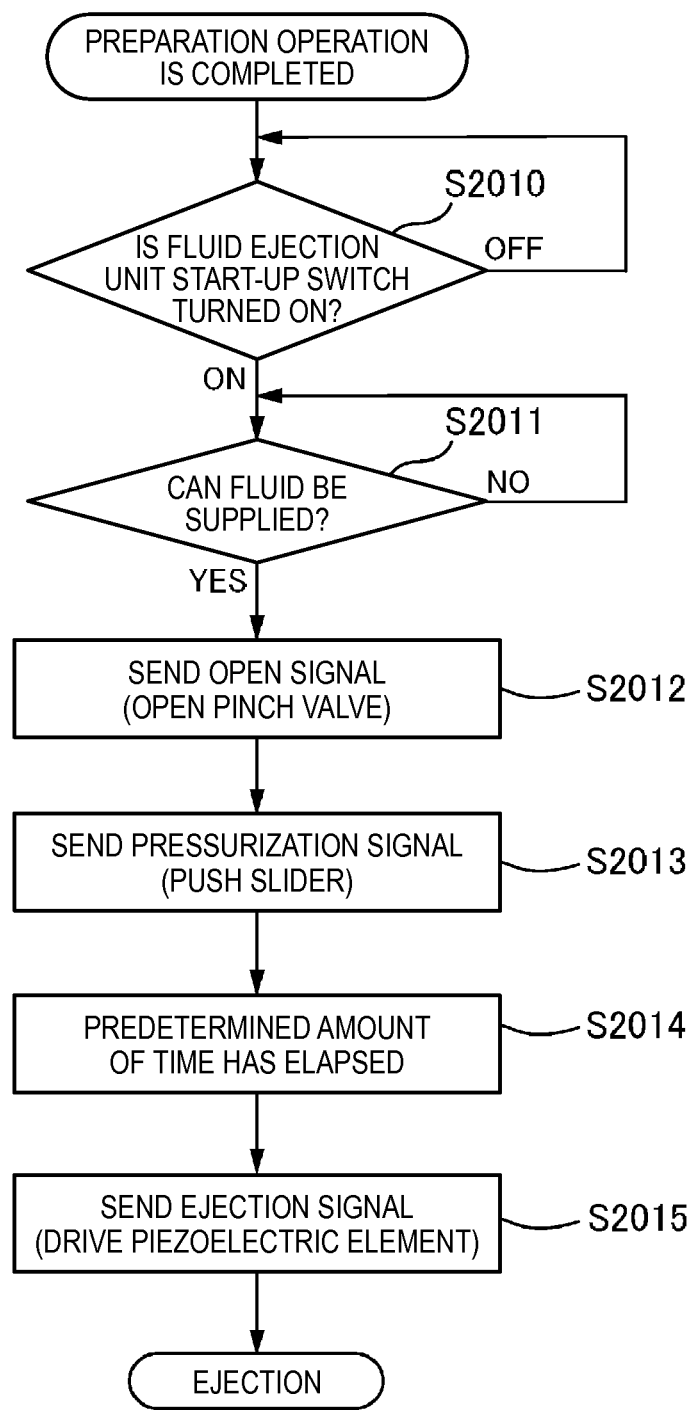
FIG. 9 is a flowchart illustrating an ejection operation of the fluid ejection device according to the embodiment of the invention.

Subsequently, FIG. 9 is a flowchart illustrating an ejection operation of the fluid ejection device according to the embodiment, and the drive control unit 600 and the pump control unit 710 controls the ejection operation of the fluid ejection device 1.

First, when a practitioner turns on the fluid ejection unit start-up switch 625, the drive control unit 600 receives a fluid supply signal (S2010), and the drive control unit 600 determines whether the fluid in the fluid accommodation portion 765 can be supplied (S2011).

When the fluid in the fluid accommodation portion 765 cannot be supplied, the drive control unit 600 does not send an open signal for opening the pinch valve 750 to the pump control unit 710.

When the fluid in the fluid accommodation portion 765 can be supplied, the drive control unit 600 sends an open signal for opening the pinch valve 750 to the pump control unit 710, and the pump control unit 710 opens the pinch valve 750 (S2012).

The pump control unit 710 sends a pressurization signal after the pinch valve 750 is opened, and thereby the slider 720 moves in the push-in direction at the predetermined speed, for the predetermined amount of time, or by the predetermined distance, all of which are pre-stored, and the fluid in the fluid accommodation portion 765 is supplied to the fluid chamber 501 in the fluid ejection unit 100 (S2013).

When the slider 720 is pushed due to the pressurization signal at the same time when the pinch valve 750 is opened or before the pinch valve 750 is opened, a discharge pressure of the pump 700 increases temporarily, and in contrast, in the embodiment, since the slider 720 is pushed due to the pressurization signal sent after the pinch valve 750 is opened, it is possible to reduce the discharge pressure that may increase temporarily.

When the fluid is supplied from the fluid accommodation portion 765, and thereafter, a predetermined amount of time has elapsed (S2014), the drive control unit 600 sends an ejection signal for ejecting the fluid to the fluid ejection unit 100 (S2015). When the piezoelectric element 401 receives the ejection signal, the piezoelectric element 401 changes the volume of the fluid chamber 501 via the diaphragm 400 through the extension and contraction thereof. The fluid is discharged in a pulsed manner to the outlet channel 511 due to a change in the volume of the fluid chamber 501, and the fluid is ejected out of the fluid ejection opening 212 via the nozzle 211. In the embodiment, since the ejection signal is sent to the fluid ejection unit 100 when the fluid is supplied from the fluid accommodation portion 765, and thereafter, the predetermined amount of time has elapsed, the fluid is not ejected at the same time when the fluid is supplied from the pump 700. Accordingly, it is possible to prevent a temporary increase in the pressure of an ejected fluid.

In a case where the ejection signal is sent when a time 100 milliseconds has elapsed after the open signal is sent, the fluid is supplied from the pump 700 at a time different from when the fluid is ejected from the fluid ejection unit 100. Accordingly, it is possible to prevent the generation of an ejection force originating from a temporarily high pressure fluid. In this manner, the fluid is ejected by the fluid ejection device 1.

Figure 10:
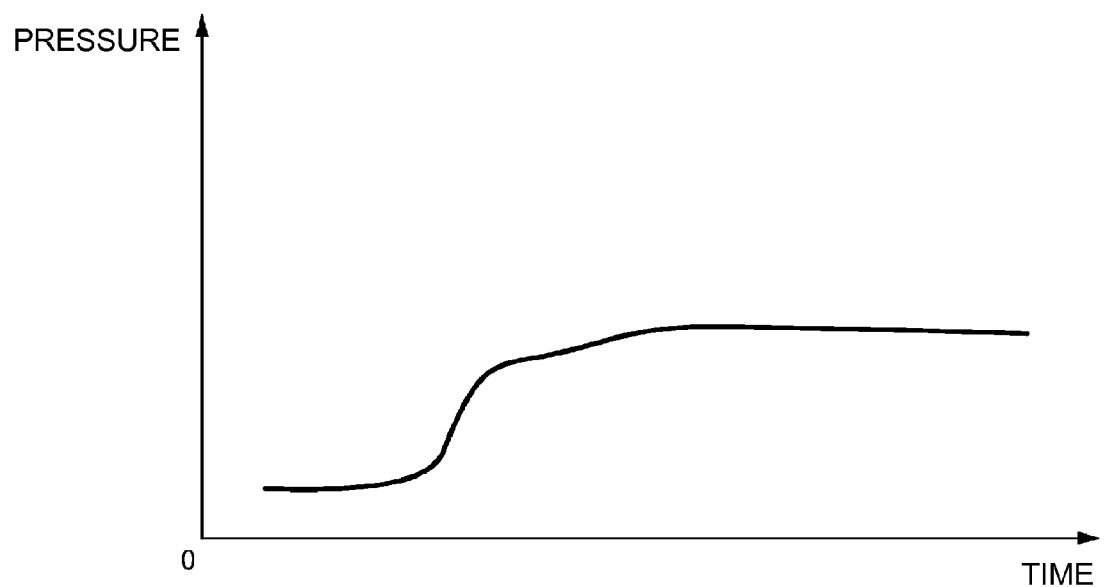
FIG. 10 is a graph illustrating a change in the pressure of the fluid ejected by the fluid ejection device according to the embodiment of the invention.
Figure 11:
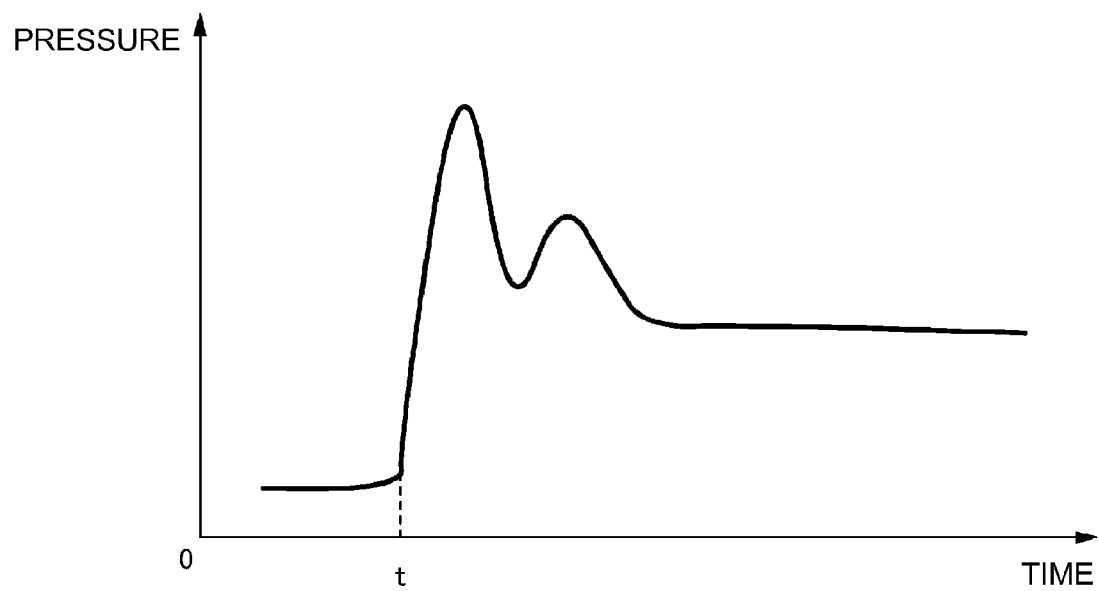
FIG. 11 is a graph illustrating a change in the pressure of the fluid ejected by a fluid ejection device in the related art.

FIG. 10 is a graph illustrating a change in the pressure of the fluid ejected by the fluid ejection device according to the embodiment. In the embodiment, since the ejection signal is sent to the fluid ejection unit 100 when the predetermined amount of time has elapsed after the drive control unit 600 sends the open signal to the pump control unit 710, the piezoelectric element 401 is not started up at the same time when the pinch valve 750 is opened, and an increase in the pressure of an ejected fluid is gently changed compared to the pressure of an ejected fluid by a fluid ejection device in the related art illustrated in FIG. 11, and thereby it is possible to reduce an ejection force unintended by the practitioner in ejecting the fluid.

Thereafter, when the practitioner turns off the fluid ejection unit start-up switch 625, the drive control unit 600 receives an OFF signal, and sends the OFF signal to the fluid ejection unit 100 and the pump control unit 710. The fluid ejection unit 100 stops the driving of the piezoelectric element 401 in response to the OFF signal, and when the pump control unit 710 receives the OFF signal, the pump control unit 710 stops the slider 720, and closes the pinch valve 750.

Second Embodiment

In the above-mentioned embodiment, the open signal is sent, and thereafter the pressurization signal is sent, and thus the slider 720 is pushed; however, the pressurization signal may be sent at the same time when or before the open signal is sent.

Also, in this case, when the open signal is sent, and thereafter the ejection signal is sent, it is possible to reduce the ejection of the fluid associated with a temporary high pressure.

Since the slider 720 is pushed due to the pressurization signal sent after the open signal is sent, it is possible to reduce the fluid from being supplied at a temporarily high pressure.

Third Embodiment

In the above-mentioned embodiment, the pump control unit 710 controls the inner pressure of the fluid accommodation portion 765 to be in the fine window, and when the inner pressure of the fluid accommodation portion 765 is in the rough window, the pump control unit 710 can send the open signal to send the fluid, and the drive control unit 600 can send the ejection signal to eject the fluid; however, it is not always necessary to control the inner fluid pressure of the fluid accommodation portion 765 to be in the fine window, and even when the inner fluid pressure of the fluid accommodation portion 765 is not in the rough window, the control units (600 and 710) may send the open signal and the ejection signal.

Also, in this case, it is possible to reduce the ejection of the fluid associated with a temporary high pressure.

In a case where the inner fluid pressure of the fluid accommodation portion 765 is controlled to be in the fine window, and the open signal and the ejection signal are sent when the inner fluid pressure of the fluid accommodation portion 765 is in the rough window, the pressure of the fluid becomes a pressure more suitable for the ejection of the fluid, and it is possible to eject the fluid with a proper ejection force.

Fourth Embodiment

In the above-mentioned embodiment, even though the drive control unit 600 receives the fluid supply signal, the open signal is not sent when the inner fluid pressure of the fluid accommodation portion 765 is not the predetermined pressure ($P_B$) or higher; however, even though the inner fluid pressure of the fluid accommodation portion 765 is not the predetermined pressure ($P_B$) or higher, the open signal may be sent when the drive control unit 600 receives the fluid supply signal.

Also, in this case, it is possible to reduce the ejection of the fluid associated with a temporary high pressure.

In a state where the drive control unit 600 receives the fluid supply signal, and the inner fluid pressure of the fluid accommodation portion 765 is the predetermined pressure ($P_B$) or higher, when the open signal is sent, it is possible to obtain an ejection force more suitable for the ejection of the fluid.

Fifth Embodiment

In the above-mentioned embodiment, before the open signal is sent, the connection tube 25 is filled up with the fluid (the priming process), and after the fluid ejection unit 100 ejects the fluid (the flushing process), the inner fluid pressure of the fluid accommodation portion 765 is controlled to be the predetermined pressure ($P_B$) or higher (the pressure control process); however, the priming process, the flushing process, and the pressure control process may not be necessarily performed.

Also, in this case, it is possible to reduce the ejection of the fluid associated with a temporary high pressure.

It is possible to reduce air in the connection tube 25 or air bubbles in the fluid from adversely affecting the ejection of the fluid by performing the priming process and the flushing process, and it is possible to obtain an ejection force more suitable for the ejection of the fluid by controlling the pressure of the fluid which is changed due to the priming process and the flushing process.

Sixth Embodiment

In the above-mentioned embodiment, the fluid ejection unit 100 ejects the fluid using the piezoelectric element 401 configured to be deformed in response to a change in voltage; however, the method of ejecting the fluid is not limited to the use of the piezoelectric element, and the fluid ejection unit 100 may eject the fluid in a pulsed manner using air bubble generation unit such as a heat generating electrode or a laser irradiator.

The fluid ejection device can also reduce a high ejection force using the piezoelectric element.

Others

The embodiments are presented so as to help the understanding of the invention, and do not limit the interpretation of the invention. Modifications and improvements can be made to the invention insofar as the modifications and the improvements do not depart from the spirit of the invention, and the equivalents are also included in the invention.

What is claimed is:

1. A fluid ejection device comprising:
   a fluid ejection unit that ejects a fluid in a pulsed manner;
   a fluid accommodation portion configured to accommodate the fluid at a predetermined pressure or higher;
   a fluid supply unit that supplies the fluid accommodated in the fluid accommodation portion to the fluid ejection unit;
   a connection channel that connects the fluid ejection unit and the fluid accommodation portion, and acts as a channel through which the fluid flows;
   an opening and closing unit that opens and closes the connection channel; and
   a control unit configured to send an open signal for opening the connection channel to the opening and closing unit, and send an ejection signal for ejecting the fluid to the fluid ejection unit,
   wherein the control unit sends the ejection signal after a predetermined amount of time has elapsed from the sending of the open signal.

2. The fluid ejection device according to claim 1,
   wherein before the control unit sends the ejection signal after sending the open signal, the control unit supplies the fluid to the fluid ejection unit by driving a pressurizing unit provided in the fluid supply unit and configured to pressurize the fluid accommodation portion.

3. The fluid ejection device according to claim 1,
   wherein a target pressure is set to be higher than the predetermined pressure,
   wherein a first lower limit pressure is set to the predetermined pressure,
   wherein a first upper limit pressure is set to be higher than the target pressure,
   wherein a second lower limit pressure is set to be higher than the first lower limit pressure and lower than the target pressure, wherein a second upper limit pressure is set to be lower than the first upper limit pressure and higher than the target pressure, wherein a first pressure range is set to range from the first lower limit pressure to the first upper limit pressure, wherein a second pressure range is set to range from the second lower limit pressure to the second upper limit pressure, wherein when the target pressure is set to a center value of each of the first pressure range and the second pressure range, the control unit controls an inner fluid pressure of the fluid accommodation portion to be in the second pressure range, and wherein when the inner fluid pressure of the fluid accommodation portion is in the first pressure range, the control unit sends the open signal and the ejection signal.

4. The fluid ejection device according to claim 1, wherein the control unit sends the open signal and the ejection signal upon a condition that the control unit receives a fluid supply signal instructive of the ejection of the fluid, wherein in a case where the inner fluid pressure of the fluid accommodation portion is not the predetermined pressure or higher, even when the control unit receives the fluid supply signal, the control unit does not send the open signal, and wherein in a case where the inner fluid pressure of the fluid accommodation portion is the predetermined pressure or higher, after the control unit receives the fluid supply signal, the control unit sends the open signal.

5. The fluid ejection device according to claim 1, wherein before the control unit sends the open signal, the control unit fills the connection channel up with the fluid, and wherein after the fluid ejection unit ejects the fluid, the control unit controls the inner fluid pressure of the fluid accommodation portion to become the predetermined pressure or higher.

6. The fluid ejection device according to claim 1, wherein when the fluid ejection unit receives the ejection signal, the fluid ejection unit ejects the fluid using a piezoelectric element configured to be deformed in response to a change in voltage.

* * * * *